United States Patent [19]

Razgulov et al.

[11] 3,973,570

[45] Aug. 10, 1976

[54] SURGICAL CLIP FORMED FROM A SUTURE MATERIAL FOR END-TO-END SUTURING OF HOLLOW ORGANS ON A MANDREL

[76] Inventors: Mikhail Mikhailovich Razgulov, ulitsa, Mashinostroitelei, 32, kv. 80, Podolsk, Moskovskoi oblasti; Lidia Alexandrouna Potekhina, Mosfilmovskaya ulitsa, 27, kv. 27; Boris Fedorovich Mashinistov, Boitsovaya ulitsa, 13 korpus 1, kv. 5, both of Moscow, all of U.S.S.R.

[22] Filed: June 18, 1974

[21] Appl. No.: 480,537

[52] U.S. Cl. .............................. 128/337; 128/346
[51] Int. Cl.[2] .................. A61B 17/08; A61B 17/11
[58] Field of Search ............ 128/334 R, 334 C, 335, 128/337, 325, 346; 285/260, 382.2

[56] References Cited
UNITED STATES PATENTS

| | | | |
|---|---|---|---|
| 2,123,889 | 7/1938 | Gleason | 285/260 X |
| 2,598,901 | 6/1952 | Garland | 128/346 |
| 3,068,870 | 12/1962 | Levin | 128/337 |
| 3,258,012 | 6/1966 | Nakayama et al. | 128/334 C |

*Primary Examiner*—Dalton L. Truluck
*Attorney, Agent, or Firm*—Haseltine, Lake & Waters

[57] ABSTRACT

Surgical clip formed from a suture material, for end-to-end suturing of hollow organs on a mandrel, such as blood vessels from 4 to 10 millimeters in diameter. The clip holds a plurality of staples, each being formed as a strip bent relative to the lateral axis thereof at an angle of approximately 90° and has two arms, of which the longer one extends from the a bending line one free end while the shorter arm extends from the same line to the other free end; and respective C-shaped cylindrical cross bars on the free ends of the arms, the generators of the cylindrical cross bars being parallel to the longitudinal axes of the respective arms while the directing curves are part of a circumference with a diameter approximately equal to the outer diameter of a hollow organ to be sutured. The center of the directing curve for the longer arm is on the same side of the plane of that arm where the shorter arm is disposed, whereas the same center for the directing curve for the cylindrical shorter arm is disposed, relative to the plane thereof, on the side opposite to that where the longer arm is disposed. One arm is longer than the other by a value approximately equal to twice the wall thickness of the hollow organ being sutured. The longer arm is provided with at least one lug for securing the staples by puncturing the walls of the hollow organ. Then the lug is bent beyond the line of the suture formed between the cross bars, thereby adding to the strength of the sutured portion of the hollow organ. The shorter arm has an expanding portion for secure fixation of the staples in the mandrel.

1 Claim, 18 Drawing Figures

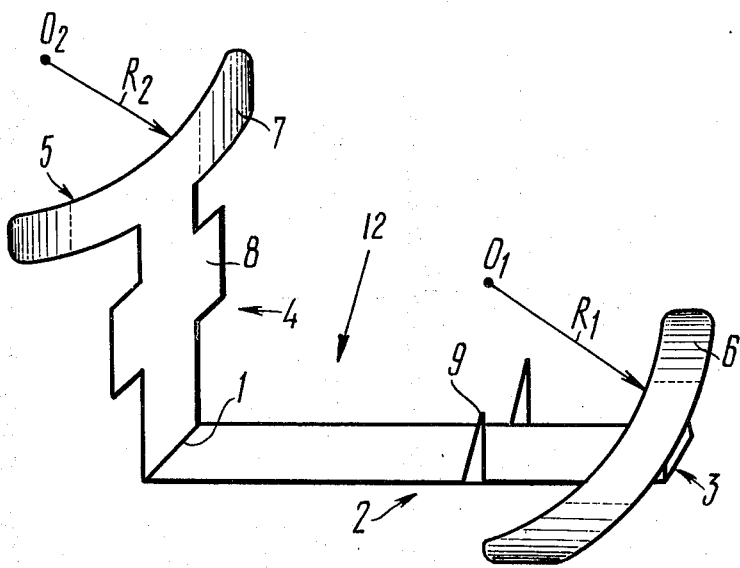
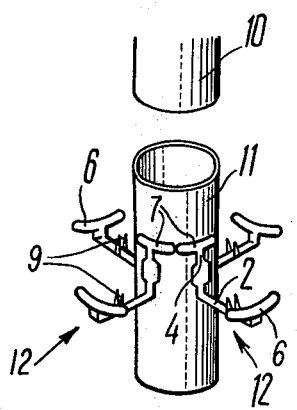 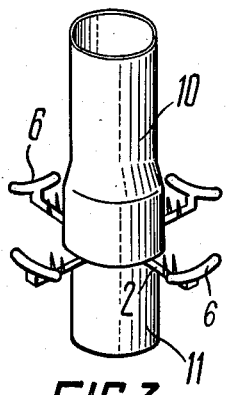 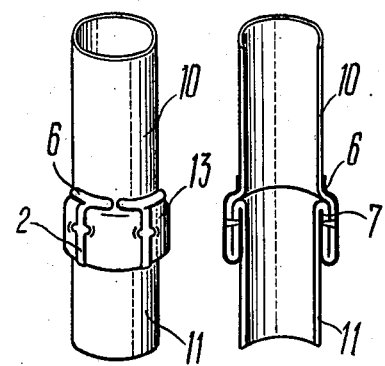
FIG.1   FIG.2   FIG.3   FIG.4   FIG.5

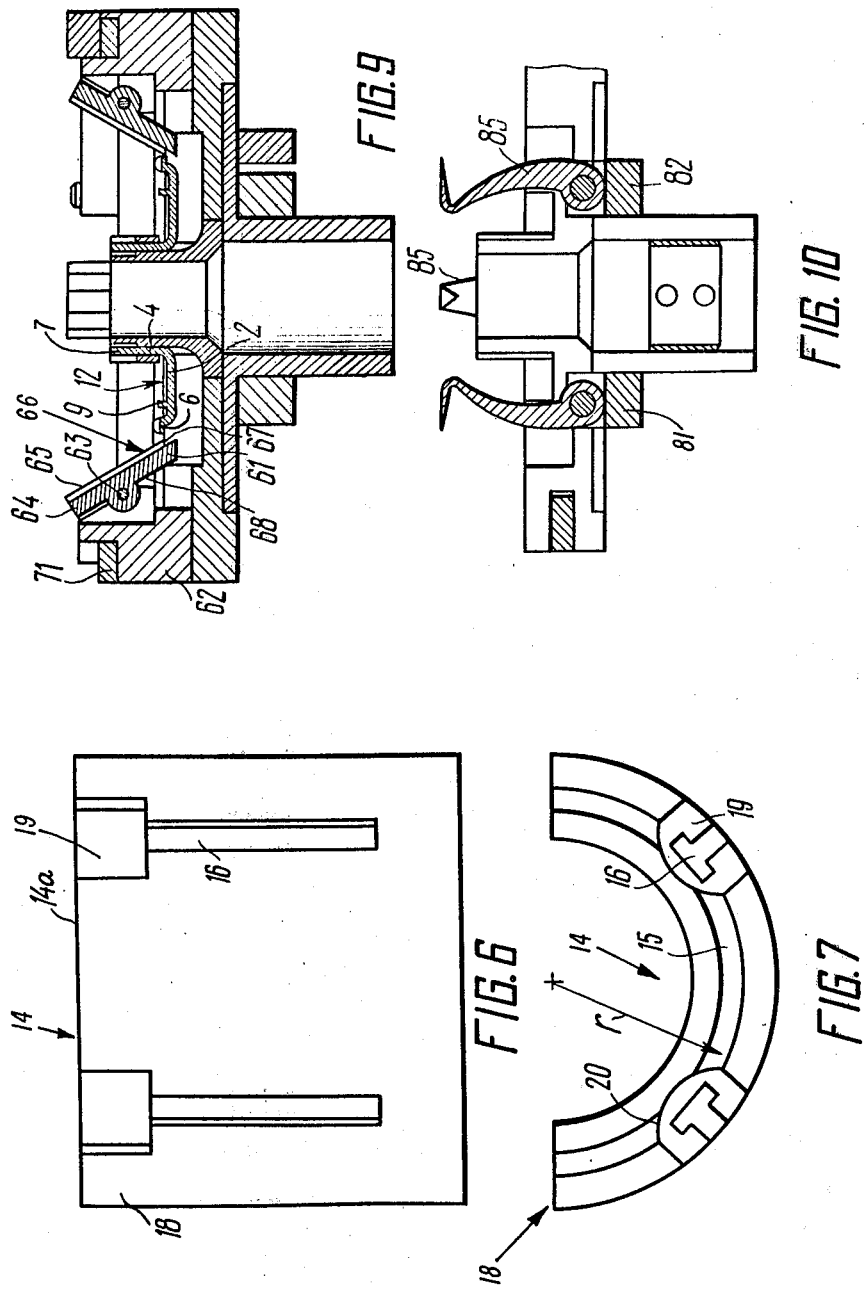

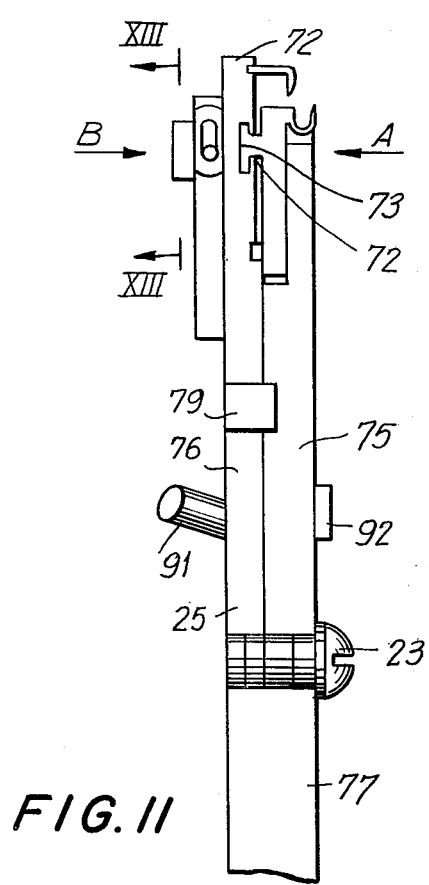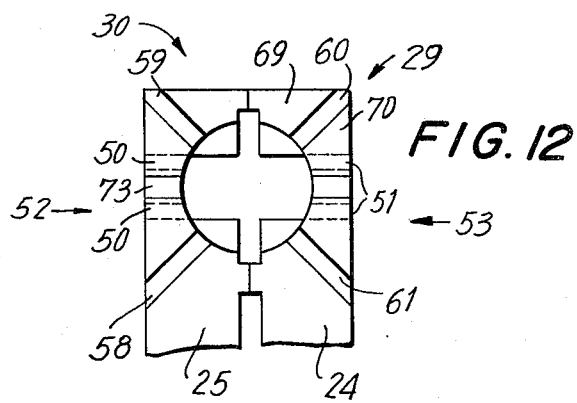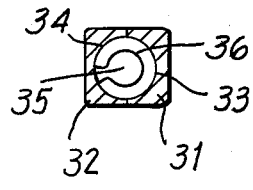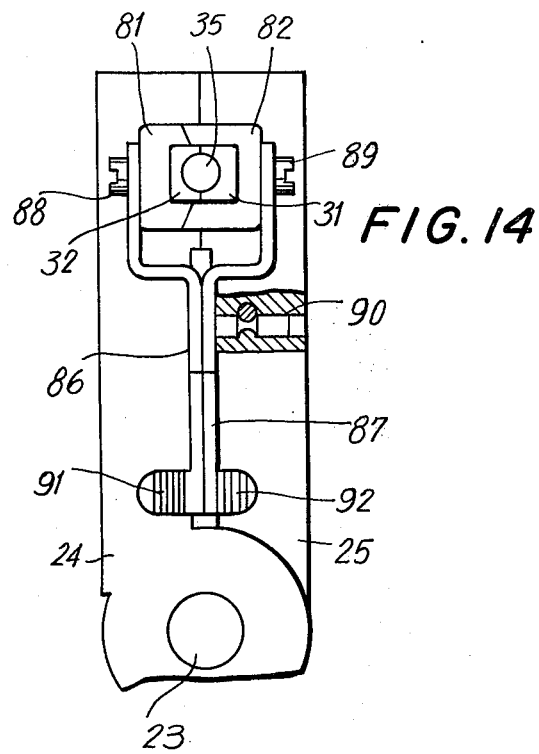

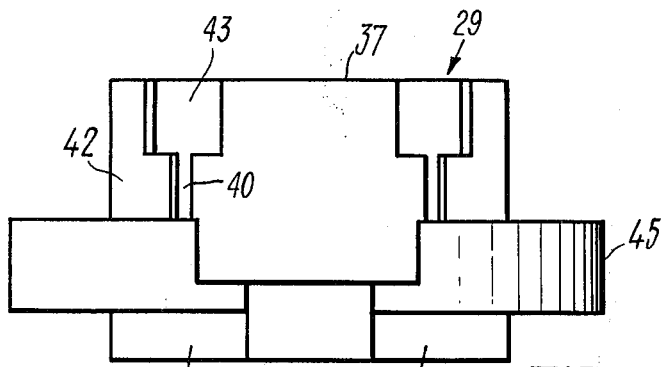
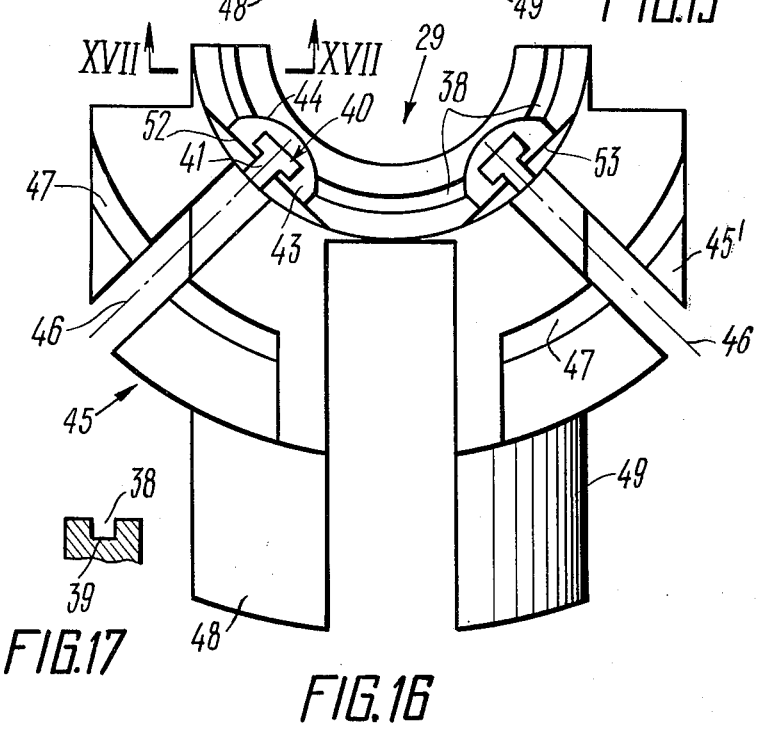

SURGICAL CLIP FORMED FROM A SUTURE MATERIAL FOR END-TO-END SUTURING OF HOLLOW ORGANS ON A MANDREL

The present invention relates to the field of medicine and more particularly to surgery; more specifically still, it relates to suture material in the form of clips for end-to-end suturing of hollow organs on a mandrel that corresponds to such suture material. The invention also describes a surgical instrument for suturing blood vessels including such a mandrel, the vessels having diameters between 4 and 10 millimeters, and corresponding wall thicknesses known to be less than one millimeter.

Surgeons in general and vascular surgeons in particular give special attention to suturing the ends of vessels which, naturally, belong in the category of hollow organs, as well as in implanting biological grafts and various vascular prostheses.

The quality of the vascular suture by and large depends on the kind of the suture material used. It is known in the art to employ a wide range of suture materials. Thus, wide use is made of silk, capron and catgut threads with which vascular sutures are applied by hand with the help of traumatic or other needles.

The application of a vascular suture with the use of such threads requires high skill and much experience on the part of the surgeon. Moreover, even a skilfully applied vascular suture using said threads has a number of serious disadvantages related to the suture material itself which as often as not leads to complications, sometimes extremely grave.

The main disadvantages of the known suture materials are as follows:

the vascular wall and the intima are inevitably traumatized (punctured) on the suture line;

stretching of the vessel ends interferes with the suture water-tightness, and the stronger the stretching the greater is the danger;

the suture material lies on the suture line and comes into direct contact with the blood flow; and due to the uneven suture application on the vascular walls "whirl pockets" are likely to arise in the vascular lumen, giving rise to a turbulent blood flow.

Each of the above disadvantages, in its turn, contributes to thrombus formation on the suture line with all the grave consequences that this implies.

Another type of suture material which has been steadily gaining ground in recent years is one formed as a plurality of staples.

At present, U-shaped metal staples with which vessels are sutured on a corresponding mandrel with special instruments are by far the most popular. These staples are made of metals of alloys neutral to live tissues.

A great range of instruments has already been developed, which considerably facilitate and speed up the suturing of the vessel ends with the suture material in the form of a plurality of said U-shaped metallic staples, so that the vessel suturing operation has come within the scope of a greater number of surgeons.

However, this suture material is not devoid of certain drawbacks inherent in the hand-applied thread suture either, viz. traumatization of the vascular walls on the suture line, which are pierced by the staples; deterioration of the suture water-tightness when the sutured vessel undergoes stretching; formation of whirl pockets; presence of the suture material on the suture line.

It is also known in the art to make use of some adhesives for obtaining vascular union. However, the latter suture material has made no inroads to speak of into vascular surgery, since adhesives cause substantial inflammations; besides, numerous experts maintain that adhesives are an insecure material for joining vessels.

Cannulas, bushings and the like have been variously tried as suture material and rejected by vascular surgeons.

The above accounts for the untiring search for a suitable suture material, which in itself emphasizes the urgency of the problem.

It is an object of the present invention to obviate the foregoing disadvantages inherent to the known suture materials.

The invention seeks to provide a novel kind of suture material or surgical clip, formed as a plurality of staples for end-to-end suturing of hollow organs on a mandrel, to provide a non-traumatizing suture; it also describes a mandrel corresponding to such suture material, and a surgical instrument for end-to-end suturing of blood vessels by means of such mandrel.

The object of this invention is attained in that a surgical clip is formed from a suture material for end-to-end suturing of hollow organs of between 4 and 10 mm diameter and a very small wall thickness on a mandrel, formed as a plurality of staples, the staples being formed as a strip bent relative to the lateral axis thereof at an angle of approximately 90°. The inventive clip comprises:

a. two arms, the longer one extending from a bending line between the arms to one free end, and the longer one extending from the same line to the other free end;

b. respective C-shaped cylindrical cross bars on the ends of each of the arms, with the generatrices of the C-shaped bars being parallel to the longitudinal axis of the arms, while the directing curves are part of a circumference with a diameter approximately equal to the outer diameter of a hollow organ to be sutured; and wherein c. the shorter arm has an expanding portion designed to provide secure fixation of the staples in the mandrel.

It is also characteristic of the invention that 1. the directing curve center of the cylindrical cross bar of the long arm is on the same side of the plane of the longer arm where the shorter arm is disposed; and 2. the directing curve center of the cross bar of the shorter arm is disposed, relative to the plane thereof on the side opposite to that where the longer arm is disposed;

3. the cross bars provide for suturing by clamping therebetween the ends of the hollow organ aligned on the mandrel;

4. the longer arm has at least one lug for fixing the staples by puncturing the walls of the hollow organ, and to be bent beyond the line of the suture formed between the cross bars, thereby adding to the strength of the sutured portion of the hollow organ; and wherein 5. one arm is longer than the other by a value approximately equal to twice the wall thickness of the hollow organ.

The invention also describes a mandrel for end-to-end suturing of hollow organs thereon with the use of the suture material in the form of a plurality of staples, constituting the surgical clip, the mandrel being preferably formed as a bushing with an annular recess formed in one of the end faces thereof, the radius and depth of the recess being approximately equal to the radius and height, respectively, of the cross bar of the shorter arm, and the annular recess having exterior longitudinal open slots the number of which slots is equal to the number of staples used to form one suture on the hollow organ being sutured. Each slot extends from the bottom of the annular recess, has a T-shaped section, and faces with its narrow portion toward the lateral surface of the bushing, with depressions being provided on the side of the lateral surface at the end face, which depressions serve as dies for bending the lugs of the longer arms of the staples.

The description also deals with a surgical instrument for end-to-end suturing of hollow organs on the described mandrel, which comprises: two branches interconnected by a pivot spindle and including working pieces and handles; the mandrel being this time made up of two half bushings mounted on the working pieces; a hemostatic clamp formed as a flat helical spring mounted on the working piece of one of the branches; slide blocks cooperating with the mandrel and reciprocably mounted on the working pieces of the branches, which slide blocks are designed for directionally bending the staples as a blood vessel is being sutured. The instrument further comprises two levers pivotally mounted on the spindle that interconnects the branches to transmit the surgeon's effort to the slide blocks while the blood vessel is being sutured; a device for everting the blood vessel which is mounted on the working pieces, the device incorporating elements to secure the ends of the blood vessel on the half bushings; and two levers which, when acted upon, provide for the eversion of the blood vessel.

It is suggested that the surgical instrument for end-to-end suturing of blood vessels be provided with grooves in the working pieces of the branches to serve as guide-paths for the slide blocks, which grooves should be disposed radially relative to the mandrel, the number of the grooves being equal to the number of staples required to form one suture.

It is likewise suggested that the surgical instrument carry on the working pieces box-section stems mounted coaxially with the half bushings, the exterior surfaces of the stems serving as guides for the device for everting the ends of the blood vessel, slidably mounted thereon, whereas the inner cavity of the stems lodge the hemostatic clamp.

The novel surgical instrument should preferably have each slide block include a case slidably mounted in one of the grooves of the working pieces and a plate pivotally mounted on the casing and including a guide slot for staples which plate is designed for bending the longer arms of the staples as the blood vessel is being sutured.

The proposed suture material is free from the drawbacks inherent to the known types of suture material.

Relatively simple and cheap, the surgical clip formed from the proposed suture material provides a non-traumatized, secure and water-tight suture in hollow organs. The staples of the suture material do not puncture the vascular walls on the suture line; the staples are fixed on the vessel being sutured by puncturing the vascular walls beyond the suture line, which in no way affects the process of healing of the vascular walls and cannot cause thrombus formation. On stretching of the ends of the sutured vessel, the suture formed by the proposed suture material, far from losing its water-tightness, even increases it somewhat due to the compression of the vessel walls.

Besides, the suture material of this invention does not project into the vascular lumen, as is the case with all known materials, and, consequently, does not interact with the blood flow as an alien body, thereby totally obviating the possibility of thrombus formation due to this particular cause. Along with the aforementioned advantages, the proposed suture material offers all the advantages inherent to the prior suture materials formed as U-shaped staples. The staples of the proposed surgical clip are made of a material inert toward live tissues and cause no inflammatory process in the affected organism.

The staple suture is intermittent and does not prevent vessel growth, which is of particular importance in pediatric surgery. The suture formed by the proposed suture material gives rise to no whirl pockets due to the presence of cross bars on the staples; hence, no conditions are provided for blood flow turbulence and no thrombus formation can occur due to this cause.

The staple design of the invention permits creating a simple and reliable instrument for blood vessel suturing with a corresponding mandrel, the latter being used both for everting thereon the ends of the blood vessel being sutured and for carrying thereon the staples of the suture material in a number required to apply one suture. One of the preferred embodiments of the proposed surgical instrument for suturing thin-walled blood vessels employs replaceable mandrels each formed as a split bushing made up of two half bushings.

As distinct from the prior surgical instruments for suturing blood vessels with a suture material formed by U-shaped staples, the proposed instrument is easy to handle, need not be dismantled before suturing a blood vessel, nor for cleaning or washing, and looks like a common surgical clamp.

The invention will be better understood from the following description of exemplary embodiments of staples constituting the suture surgical clip made from the material of the invention, a corresponding mandrel, and a surgical instrument for suturing blood vessels incorporating this mandrel, taken in conjunction with the accompanying drawings, wherein FIG. 1 is a general view of a suture staple to be formed into a surgical clip in accordance with the invention;

FIG. 2 is a general view of the layout of staples relative to a thin-walled hollow organ to be sutured at the beginning of the suturing process;

FIG. 3 is a general view of FIG. 2 with the hollow organ to be sutured everted;

FIG. 4 is a general view of the sutured hollow organ;

FIG. 5 is a longitudinal sectional view of FIG. 4;

FIG. 6 is a side elevation of a half bushing;

FIG. 7 is a plan view of FIG. 6;

FIG. 8 is a plan view of a surgical instrument for suturing blood vessels in accordance with the invention;

FIG. 9 is a sectional view taken in the plane IX—IX of FIG. 8;

FIG. 10 is a sectional view taken in the plane X—X of FIG. 8;

FIG. 11 is the partial side elevation of a surgical instrument of FIG. 8;

FIG. 12 is a view of the instrument shown in FIGS. 8 and 11, taken along the arrow A in the latter, with half bushings, slide blocks, pushers and an eversion unit shown dismantled;

FIG. 13 is a sectional view taken in the plane XIII—XIII of FIG. 11;

FIG. 14 is a view of the instrument of FIGS. 8, 11 and 12 taken along the arrow B;

FIG. 15 is a side elevation of another half bushing of a surgical instrument for suturing blood vessels;

FIG. 16 is a plan view of the half bushing shown in FIG. 15; and

FIG. 17 is a sectional view taken in the plane XVII—XVII of FIG. 16.

Figure 8A:
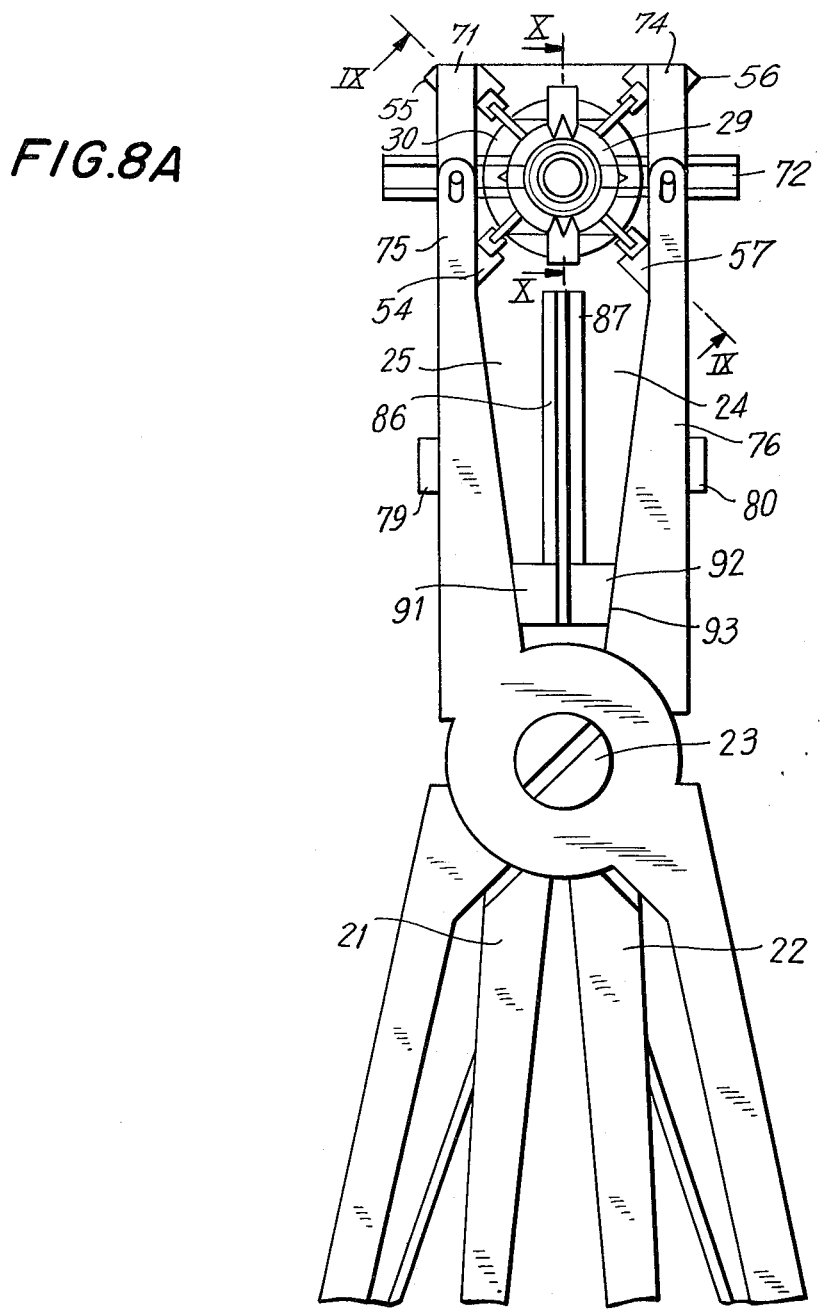
FIG. 8A is a large-scale view corresponding to the top portion of FIG. 8, the bottom having been broken away.

The surgical clip formed from a suture material in accordance with the invention comprises a plurality of staples each of which in the embodiment illustrated herein is formed as a metal strip bent relative to the lateral axis thereof, thus forming a bending line 1 (FIG. 1). The staples can also be made of any other material exhibiting the required physical and mechanical properties, e.g. plastics inert toward live tissues, or combinations of plastics with metals or metal alloys. The staple has a longer arm 2 extending from the line 1 to a free end 3 and a shorter arm 4 extending from the same line 1 where the arms 2, 4 are bent to the other free end 5 of the staple.

The free end 3 of the longer arm 2 of the staple carries a C-shaped cylindrical cross bar 6. It is common knowledge that the generatrix of a cylindrical surface is a straight line which is displaced parallel to itself, all the time intersecting a predetermined line known as the directing curve for this cylindrical surface.

The generatrix of the C-shaped cylindrical cross bar 6 is parallel to the longitudinal axis of the arm 2. The center $0_1$ of the directing curve is disposed on the same side of the plane of the longer arm 2 as that where the shorter arm 4 is disposed, the directing curve being part of a circumference of diameter $D_1 = 2R_1$ approximately equal to the diameter of the hollow organ to be sutured.

The free end 5 of the shorter arm 4 of the staple also has a C-shaped cylindrical cross bar 7, whereof the generatrix is parallel to the longitudinal axis of this arm 4.

The center $0_2$ of the directing curve is disposed, relative to the plane of this shorter arm 4, on the side opposite to that where the longer arm 2 is disposed, and the directing curve is part of a circumference of diameter $D_2 = 2R_2$ approximately equal to the diameter of the hollow organ to be sutured. Obviously, the radii of curvature $R_1$ $R_2$ of the respective cross bars of the shorter and the longer arms are equal.

The cylindrical cross bar 6 of the longer arm 2 in this staple embodiment is displaced parallel to itself relative to the plane of the arm 2 toward the center $0_1$ by a distance approximately equal to twice the wall thickness of the hollow organ to be sutured. It is well known to those skilled in the art that hollow organs, such as blood vessels, ranging between 4 and 10 millimeters, usually have wall thicknesses that are less than 1 millimeter.

This design of the cross bars 6 and 7 ensures suturing of the hollow organ with the ends of the latter aligned on a corresponding mandrel clamped between the cross bars 6 and 7.

The shorter arm 4 has an expanding portion 8, whereby the staple is securely fixed in the mandrel.

The longer arm 2 comprises two lugs 9, whereby said staple is fixed on the sutured hollow organ, with the lugs puncturing the walls of the hollow, and to be bent beyond the line of the suture formed between said C-shaped cylindrical cross bars 6 and 7. Thereby the sutured section of the hollow organ is rendered stronger.

The arm 2 is longer than the arm 4 by a value approximately equal to twice the above-mentioned average wall thickness of the hollow organ being sutured.

To give a better idea of the design features of the proposed suture material and surgical clip made therefrom as well as of the purpose of all its elements, let us discuss the process of hollow organ suturing. Prior to the start of suturing, ends 10 and 11 (FIG. 2) of the hollow organ to be sutured are aligned one opposite the other. In the case described, four staples 12 are used to form one suture. These four staples 12 are arranged at regular intervals on a mandrel around the end 11 of the hollow organ to be sutured.

After eversion, when the end 11 is turned with the intima outward to form a vascular cuff and pulled over the mandrel to envelop the shorter arms 4 of the staples 12 while the end 10 is pulled over the end 11 (FIG. 3), the longer arms 2 of the staples 12 are simultaneously bent to form a non-traumatized suture 13 (FIGS. 4 and 5) between the cross bars 6 and 7, and the lugs 9 securely fix the staples on the sutured hollow organ.

In the course of the above process, as can be clearly seen in FIG. 5, the lugs 9 puncture the walls of the ends 10 and 11 of the hollow organ beyond the suture line, improving the strength of the sutured section but in no way detracting from the quality of the suture.

The mandrel corresponding to the above-described suture material is formed in one possible embodiment as a split bushing 14 made up of two half bushings. An annular recess 15 is formed in one of the end faces 14 (FIGS. 6 and 7) of each half bushing, the radius $r$ of the annular recess 15 being equal to the radius $R_2$ of said cross bar 7 of the shorter arm 4 of the staple, while the depth of the annular recess 15 is equal to the height of that same cross bar 7.

In the exterior surface of the half bushing 14 there are formed longitudinal open slots 16 each of which starts at the bottom of the annular recess 15, has a T-shaped cross-section and faces with the narrow portion thereof toward the lateral surface 18 of the half bushing of the mandrel. On the side of this lateral surface 18 at the end face 14a there are provided depressions 19. Each depression 19 has a wall 20 of such a shape that after the lugs puncture the walls of the hollow organ, as the latter is being sutured, beyond the suture line the lugs are bent, thereby securely fixing the staples on the sutured hollow organ and improving the strength of the sutured section of the hollow organ.

The mandrel formed as a split bushing that can be taken apart into two half bushings is one of the possible embodiments. Depending on the specific circumstances, an integral bushing may be employed provided it exhibits all the essential features described among the subjects of the invention and in the specification.

If the mandrel is formed as a split bushing, the half bushings making up the bushing may be either identical or differing in size (one larger, the other smaller) depending on whether the plane of the joint of the bushing passes through its longitudinal axis or is shifted relative to this longitudinal axis.

It can be seen from the specification and accompanying drawings that the proposed exemplary mandrel fully conforms to the design of the proposed suture material and can be employed for suturing hollow organs thereon only with the proposed suture material.

Depending on the design of the mechanism for directional bending of the staples in the course of suturing or depending on the design of the stapler used, the proposed mandrel may be additionally equipped with appropriate structural elements which, naturally, may be constructed in a great range of designs determined by the type of the mechanism or stapler wherein the proposed mandrel is to be employed.

While preparing for surgery, the staples of the proposed suture material are mounted in the longitudinal slots 15, with the shorter arm 4 of the staple disposed in the expanding portion of the T-shaped slot 16 and the longer arm 2 of the staple projecting outward through the narrow open portion of the slot. The T-shaped configuration of the slot and the expanding portion 8 of the shorter arm of the staple provided for the secure fixation of the staples on the half bushings 14.

The mandrel described hereabove, designed for end-to-end suturing thereon of hollow organs with the proposed suture material, formed as a plurality of staples and comprising a bushing made up of two half bushings, is an essential element which may serve as a basis for developing diverse devices, ensuring a completely mechanized process of suturing hollow organs, predominantly vessels such as thin-walled blood vessels.

The following is a description of a specific embodiment of a surgical instrument for end-to-end suturing of blood vessels comprising a mandrel of the type described hereabove.

The surgical instrument comprises two branches 21 and 22 (FIGS. 8, 8A and 11) pivotally interconnected by a pivot spindle 23. The branches 21 and 22 comprise working pieces 24 and 25, respectively, and handles 26 and 27, respectively.

There is a rack-and-pinion lock 28 to immobilize the branches in a brought-together position.

Half bushings 29 and 30 (see also element 14 in FIGS. 6 and 7) that make up the mandrel are mounted on the working pieces 24 and 25, respectively. The half bushings 29 and 30 are made in several sets of different sizes, each set corresponding to the size of the blood vessel to be sutured; the half bushings are replaceable elements of the surgical instrument under discussion.

Stem portions 31 and 32 (FIGS. 11, 13 and 14) having together a box section are rigidly secured on the branches coaxially with the half bushings 29 and 30, respectively. The stems have depressions with cylindrical lateral surfaces 33 and 34, respectively, which define, with the stems 31, 32 brought together, a circular opening 35.

A hemostatic clamp formed as a flat helical spring 36 is secured in one of the stem portions 31, 32 (see FIG. 13).

For the sake of clarity, FIGS. 8A and 11 through 14 are presented on a larger scale then the other illustrations. FIG. 8A of course constitutes a duplication of the overall plan view of the instrument shown in FIG. 8.

An annular recess 38 is provided in the end face 37 (FIGS. 15 – 17) of each half bushing 29 and 30.

Longitudinal open T-shaped slots 40, whereof a narrow portion 41 faces toward a lateral surface 42 of the half bushing, extend from the bottom 39 of the annular recess 38 (see FIGS. 15–17).

On the side of the lateral surface 42, in the upper portion of the half busing, at the end face 37 thereof, there are provided depressions 43, each located at the site where the slots 40 are disposed. The shape of walls 44 of the depression 43 is so selected that as the lugs of the staple puncture the walls of the blood vessel being sutured these lugs are sure to be bent.

In fact each portion of the half bushing 29 or 30 with a depression 43 is a die, and the wall 44 of this depression serves as the working face of the die, whereby the lugs of the staple are bent to fasten the walls of the blood vessel being sutured beyond the suture line. The half bushings incorporate flanges 45 with slots 46 and an annular recess 47 as well as stems 48 and 49. Part 45' will be described later.

The elements 45 – 49 are designed, above all, to provide for the mounting of the half bushings 29, 30 on the respective working pieces 24 and 25 of the branches 21 and 22, as well as for the required degree of cooperation between the half bushings 29 and 30 and the other members of the surgical instrument being described in the course of blood vessel suturing.

Each of the half bushings 29 and 30 is mounted by way of the stems 48 and 49 into respective slots 50 and 51 (FIG. 12) of the working pieces 24 and 25 of the branches 21 and 22.

The annular recess 47 makes it more convenient to grip the end of the vessel to be everted.

There are flats 52 and 53 (see FIG. 16) provided on the exterior surfaces of the half bushings which ensure full bending of the lugs of the staples of the suture material.

The half bushings 29 and 30 (FIG. 8) may be made of plastics, e.g. polycarbonate (commercially known under the trade designation "Diflen"), or stainless steel. Made of plastics, the half bushings may be both disposable or designed for multiple use.

A set of replaceable half bushings enables thin-walled blood vessels from 4 to 10 mm in diameter to be sutured with the same surgical instrument.

To bend the staples of the suture material, which are mounted in the slots 40 of the half bushings 29 and 30 that make up the mandrel, there are provided reciprocably mounted slide blocks 54, 55, 56 and 57 cooperating with the mandrel (the slide blocks 54 and 55 cooperate with the half bushing 30 of the mandrel, while the slide blocks 56 and 57 cooperate with the half bushing 29. There are evenly spaced grooves 58, 59, 60 and 61 (FIG. 12) formed in the working pieces 24 and 25 of the branches 21 and 22, which serve as guide grooves for the slide blocks 54, 55, 56 and 57, respectively, said guide grooves being disposed radially and symmetrically relative to the mandrel.

Each of the slide blocks 54, 55, 56 and 57 comprises a case 62 (FIG. 9) slidably mounted in the respective guide groove 58, 59, 60 or 61 and a plate 64 pivotally mounted on the case 62 by means of a pivot 63, the plate 64 having a guide slot 65 for the respective staple. The plate 64 directly cooperates with the longer arm 2 of the staple while a blood vessel is being sutured, thereby providing for directional bending of the staple arm.

The plate 64 has a guide boss 66 and shoulders 67 whereof the lower planar faces are inclined to the lateral surface 68 of the plate 64.

The guide slot 65 of the plate 64 prevents transversal displacement of the respective staple in the course of suturing.

In the initial position, the shoulders 67 rest on surfaces 69 and 70 of the working pieces 24 of the branch 21, whereas the guide boss 66 is disposed in the groove 60 of the working piece 24.

There is a longitudinal groove parallel to the longitudinal axis of the instrument formed in the slide block, which receives the end of a pusher 71. The pusher 71 is formed as a plate, in the middle of which and normal thereto there is secured an elongated T-shaped guide 72 slidably mounted in a groove 73 formed in the working piece 25 of the branch 22.

All in all, there are two pushers of which one, 71, is shown linked with the working piece 25, while the other, 74, is linked with the working piece 24 of the branch 21.

Each of the pushers is in engagement with two slide blocks and is coupled with a respective suturing lever 75 or 76, pivotally mounted on the pivot spindle 23, whereby the branches 21 and 22 are interconnected. Handles 77 and 78 of the respective suturing levers 75 and 76 are spring-loaded and disposed in the tail portion of the instrument where the handles 26 and 27 are likewise disposed.

There are stops 79 and 80 secured on the lateral surfaces of the branches 22 and 21, respectively, which serve to limit the extent of displacement of the suturing levers 75 and 76.

The instrument for suturing blood vessels also comprises a device for everting the ends of the blood vessel to be sutured.

This eversion device comprises two asymmetrical split casings 81 and 82 (FIGS. 10, 14, the latter being reversed left-to-right by comparison with FIG. 8) movably mounted on the stems 31 and 32 disposed on the working pieces 24 and 25 of the branches 21 and 22, respectively.

One casing, 82, carries three pivotally mounted swivelling lugs 85, while the other casing, 81, carries one such swivelling lug, likewise pivotally mounted on the casing.

The swivelling lugs 85 permit replaceable half bushings (e.g. 29, 30) of various sizes to be used, thereby considerably expanding the functional potential of the instrument.

The casings 81 and 82 are kinematically linked with eversion levers 86 and 87, respectively, by means of screws 88 and 89.

The eversion lever 86 is movably mounted on the working piece 25 of the branch 22 by means of a pivot spindle 90, while the eversion lever 87 is movably mounted on the working piece 24 of the branch 21 by means of a pivot spindle similar to 90. The levers 86 and 87 are also provided with bearing members 91 and 92.

The upper bearing member 91 has an inclined surface 93, the angle of inclination thereof being selected so that the bearing surface 93 bears against the respective suturing lever while the lugs 85 of the eversion device are in their uppermost position, that is to say until the blood vessel to be sutured has been completely everted.

Thus, the bearing members of the eversion levers perform an additional blocking function, preventing suturing of the blood vessel with the suture material staples until the process of eversion is over.

The instrument of this invention is operated in the following manner. After the instrument has been sterilized, pressure is exerted on the upper bearing members 92 of the eversion levers 86 and 87 to move them until abutment, thereby blocking the suturing levers 75 and 76.

Then the rack-and-pinion lock 28 is unlocked and half bushings 29 and 30 of a size corresponding to the size of the blood vessel to be sutured are put into place.

These half bushings are likewise pre-sterilized, and the staples are inserted into the slots 41 of the half bushings.

Then the branches 21 and 22 are pulled apart and the instrument is brought to one of the ends of the blood vessel to be sutured so that this end of the blood vessel is disposed intermediate the half bushings 29 and 30, projecting thereabove by 3 to 4 mm.

After this, the branches 21 and 22 are brought together and the rack-and-pinion lock 23 locked, causing the hemostatic clamp 36 to elastically compress the end of the vessel and thereby check blood flow.

Then, using pincers, the vessel end is pinned on the swivelling lugs 85 of the eversion device, turning the vessel end with its intima outward so that a vascular cuff is formed, with the swivelling lugs 85 being maximally brought to the center. Such an arrangement ensures simplicity, ease and speed of the operation of vessel end pinning on the swivelling lugs 85, and, more serious still, the vascular wall is traumatized only negligibly.

The other end of the same blood vessel is pinned on the same lugs above the vascular cuff formed on the previously discussed end of the blood vessel.

After this, pressure is simultaneously exerted on both bearing surfaces 91 of the eversion levers 86 and 87, causing them to move until abutment, so that the casing 81 and 82 together with the swivelling lugs 85 move downward and the ends of the blood vessel to be sutured are stretched (everted) on the half bushings. Simultaneously the suturing levers 75 and 76 are unlocked so that they acquire mobility around the pivot 23.

The next step is suturing proper, which is effected by the surgeon by pressing on the handles 77 and 78 of the suturing levers 75 and 76.

The ends of the levers opposite to the handles 77 and 78 are caused to move toward the center of the mandrel made up of the half bushings 29 and 30, also moving the pushers 71 and 74, which are kinematically linked with the levers 75 and 76.

The slide blocks 54 and 55 kinematically linked with the pusher 71 move toward the half bushing 30, whereas the slide blocks 56 and 57 kinematically linked with the pusher 74 move toward the half bushing 29.

As each of the slide blocks 54 – 57 executes its movement, after the shoulders 67 of the plate 64 slip off a surface 45' of the respective half bushing, the plate 64 of the respective slide block turns about is pivot 63, cooperating with the longer arm 2 of the staple 12 and thereby bending the staple. In the subsequent interaction with the respective half bushing 14, the lugs of each staple bear against the wall 20 of the depression 19, puncture the walls of the ends of the blood vessel being sutured beyond the suture line, then bear against the wall 20 of the depression 19 of the respective half bushing, and are thereby bent.

As the slide blocks 54 – 57 cooperate with the respective half bushings 29 and 30, a non-traumatizing suture is being formed between the cross bars 6 and 7 of the staples 12, and the ends of the blood vessel come to be sutured together.

After this, using pincers, the vascular cuff in taken off one of the lugs 85 on the half busing 30 and, releasing the vascular cuff from this half bushing, the branches 21 and 22 are taken apart. Then, by turning the branches and using pincers, the vascular cuff is taken off the remaining lugs 85 on the half bushing 29, fully disengaging the instrument from the sutured blood vessel, whereupon the instrument is withdrawn from the surgical wound.

The foregoing specification is concerned with one of several possible embodiments of an instrument for suturing blood vessels, with the suture material in accordance with the invention, by the use of a mandrel made up of two half bushings corresponding to the suture material used. Naturally, all of the above sizes (particularly those of replaceable half bushings), recommendations as regards the steps of the blood vessel suturing operation, the relationships of individual parts, and all other detailized information relate only to the described embodiment which is just one of the possible embodiments of a vessel stapler which fall within the scope of the present invention.

Other embodiments of surgical instruments for suturing blood vessels or other hollow organs will obviously occur to those skilled in the art. An important feature of the present invention resides in that standard designs and known parts, units and kinematic links may be employed in various modifications of surgical staple-suturing instruments based on the one described hereabove.

Thus, for instance, the mandrel may be formed as a bushing with a longitudinal opening wherethrough the vessel being sutured is inserted and withdrawn, rather than as two half bushings. Besides, the mandrels may be permanent, and not replaceable, rigidly mounted on the working pieces of the branches. In the latter case each instrument will be designed for suturing vessels of a definite size, so that with such an approach a set of instruments will be practicable.

The proposed suture material and the proposed instrument for suturing thin-walled blood vessels therewith have been subjected to comprehensive experimental trials, and it has been found that the invention is instrumental in considerably facilitating and speeding up the suturing of hollow organs, including blood vessels, which means that all surgical operations associated with the need to suture hollow organs are equally considerably facilitated and speeded up thereby.

Thus, an average-skill surgeon employing the proposed surgical instrument for suturing hollow organs with the proposed suture material is able to suture one blood vessel (at one site) within 1 or 2 minutes, depending on the kind of surgical situation, with not more than half a minute devoted to the process of vessel eversion.

At the same time, a similar surgical operation performed with prior instruments for suturing blood vessels using known suture materials takes from 3 to 5 minutes, depending on the kind of surgical situation.

Experiments indicate that the proposed instrument permits suturing short vessel ends (having lengths on the order of 4 to 5 mm), whereas with all the prior-art instruments the exposed ends of the vessels to be everted and subsequently sutured have to be at least 20 mm long each. It has been further found that the proposed instrument can be employed for suturing a great variety of vessels, including the thinnest and severely sclerosed ones.

The proposed suture material has been tested in numerous trials on dogs at the Sklifasovskii First Aid Institute (Moscow) in the Organ Grafting Laboratory, with the instrument for suturing blood vessels described hereabove used throughout for suturing blood vessels on a mandrel with the suture material of this invention.

The trials were performed in extremely grave surgical situations. Thus, the operations performed included homo-transplantation of the head, kidneys, liver and a whole set of organs.

Along with sophisticated surgery, simple suturing of cut blood vessels, both arteries and veins, was also performed. All in all, at the first stage of experimentation, forty blood vessels were sutured, with the sutures being invariably of high quality and not a single case of thrombus formation registered on the suture line. At that stage the follow-up was 2 months.

Later, another series of animal experiments was undertaken which included a variety of blood vessel suturing operations with the proposed suture material on a mandrel by use of the proposed instrument.

In this latter series, out of 28 experiments (150 anastomoses) 16 were performed in the Organ Grafting Laboratory, and throughout the entire follow-up period (up to 18 months) there was not a single case of complications, or thrombus formation, or narrowing of the vascular lumen.

All the preparations from the above experiments were subjected to radiological and histological investigations which proved the high quality of the vascular sutures formed. Besides, the suture material led to the development of a simple, reliable and economical instrument for staple-suturing blood vessels which ensures fast application of a secure non-traumatizing suture and which can be handled by a medium-skill surgeon. Thus, the proposed suture material for blood vessel suturing on a mandrel and the proposed instrument employing the same fully meet the requirements of the present-day vascular surgeon.

What is claimed is:

1. A surgical clip formed from a suture material, to make an end-to-end suture on a mandrel in two axially aligned sections of a hollow organ, the latter having an outer diameter between 4 and 10 millimeters and a corresponding very small wall thickness, comprising a plurality of staples formed from pairs of sections of a strip, that are bent about a bending line, relative to a lateral axis of said strip, each staple comprising a. two arms constituted by said strip sections, extending from said bending line of the strip to respective free ends of the same staple, having different lengths, and respective planes substantially at an angle of 90° with respect to each other;

b. substantially C-shaped cylindrical cross bars for said arms on the respective free ends; cylindrical surfaces of said cross bars having straight-line generatrices that are parallel to longitudinal axes of the respective arms; the difference in length between the longer one of said arms and the shorter other arm allowing at least one of the hollow organ sections to be grasped between said cylindrical surfaces of said cross bars when the latter are folded in use into a substantially overlapping position; said generatrices continually intersecting directing curves of the respective cylindrical surfaces; said directing curves being part of a circle substantially equal to the outer diameter of the at least one hollow organ section being grasped; and c. said shorter arm having an expanding portion for secure fixation in said mandrel; wherein
   1. the center of said directing curve of the cross bar of said longer arm is on the side of the latter where said shorter arm is disposed;
   2. the center of said directing curve of the cross bar of said shorter arm is on the opposite side of the latter, where said longer arm is disposed;
   3. said cross bars provide for suturing by clamping therebetween the hollow organ sections when aligned on said mandrel and when said cross bars are folded into the overlapping position; and wherein
   4. said longer arm is provided with at least one lug for securing said staple by puncturing the wall of at least one hollow organ section, said lug to be bent beyond the line of the suture formed between said cross bars, thereby increasing the strength of the suture in the hollow organ.

* * * * *